United States Patent
Magnani et al.

(10) Patent No.: US 9,776,953 B2
(45) Date of Patent: Oct. 3, 2017

(54) ISOLATION AND PURIFICATION OF 6-AMINOCAPROIC ACID

(71) Applicant: DIPHARMA FRANCIS S.r.l., Baranzate (MI) (IT)

(72) Inventors: Massimo Magnani, Baranzate (IT); Enrico Brunoldi, Baranzate (IT); Gabriele Razzetti, Baranzate (IT); Alessandro Restelli, Baranzate (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 15/228,122

(22) Filed: Aug. 4, 2016

(65) Prior Publication Data

US 2017/0036991 A1    Feb. 9, 2017

(30) Foreign Application Priority Data

Aug. 6, 2015   (IT) .................. 102015000042906

(51) Int. Cl.
| | | |
|---|---|---|
| *C07C 227/40* | (2006.01) | |
| *C07C 227/42* | (2006.01) | |
| *C07C 229/08* | (2006.01) | |

(52) U.S. Cl.
CPC .......... *C07C 227/40* (2013.01); *C07C 227/42* (2013.01); *C07C 229/08* (2013.01)

(58) Field of Classification Search
CPC .......................... C07C 227/40; C07C 227/42
See application file for complete search history.

(56) References Cited

U.S. PATENT DOCUMENTS

| | | |
|---|---|---|
| 3,113,966 A | 12/1963 | Formaini et al. |
| 3,655,748 A | 4/1972 | Tandara |
| 8,809,581 B2 | 8/2014 | Tien et al. |
| 2014/0039219 A1 | 2/2014 | Tien et al. |

FOREIGN PATENT DOCUMENTS

| | | |
|---|---|---|
| DE | 18334 | 3/1960 |
| DE | 222008 A1 | 5/1985 |
| ES | 289989 | 7/1963 |
| RO | 96549 A2 | 3/1989 |

OTHER PUBLICATIONS

Schou-Pedersen et al., Journal of Pharmaceutical and Biomedical Analysis, vol. 107, p. 333 (2015).
Eck, £-Aminocaproic Acid, Organic Synthesis Collection, vol. 2, p. 28 (1943).
Meyers et al., £-Aminocaproic Acid, Organic Synthesis Collection, vol. 4, p. 39 (1963).

*Primary Examiner* — Golam M M Shameem
(74) *Attorney, Agent, or Firm* — Rothwell, Figg, Ernst & Manbeck, P.C.

(57) ABSTRACT

The present invention relates to a new process for the isolation and purification of 6-aminocaproic acid, which is a known inhibitor of enzymes responsible for fibrinolysis and is used in the treatment of coagulopathies and severe postoperative bleedings.

15 Claims, 1 Drawing Sheet

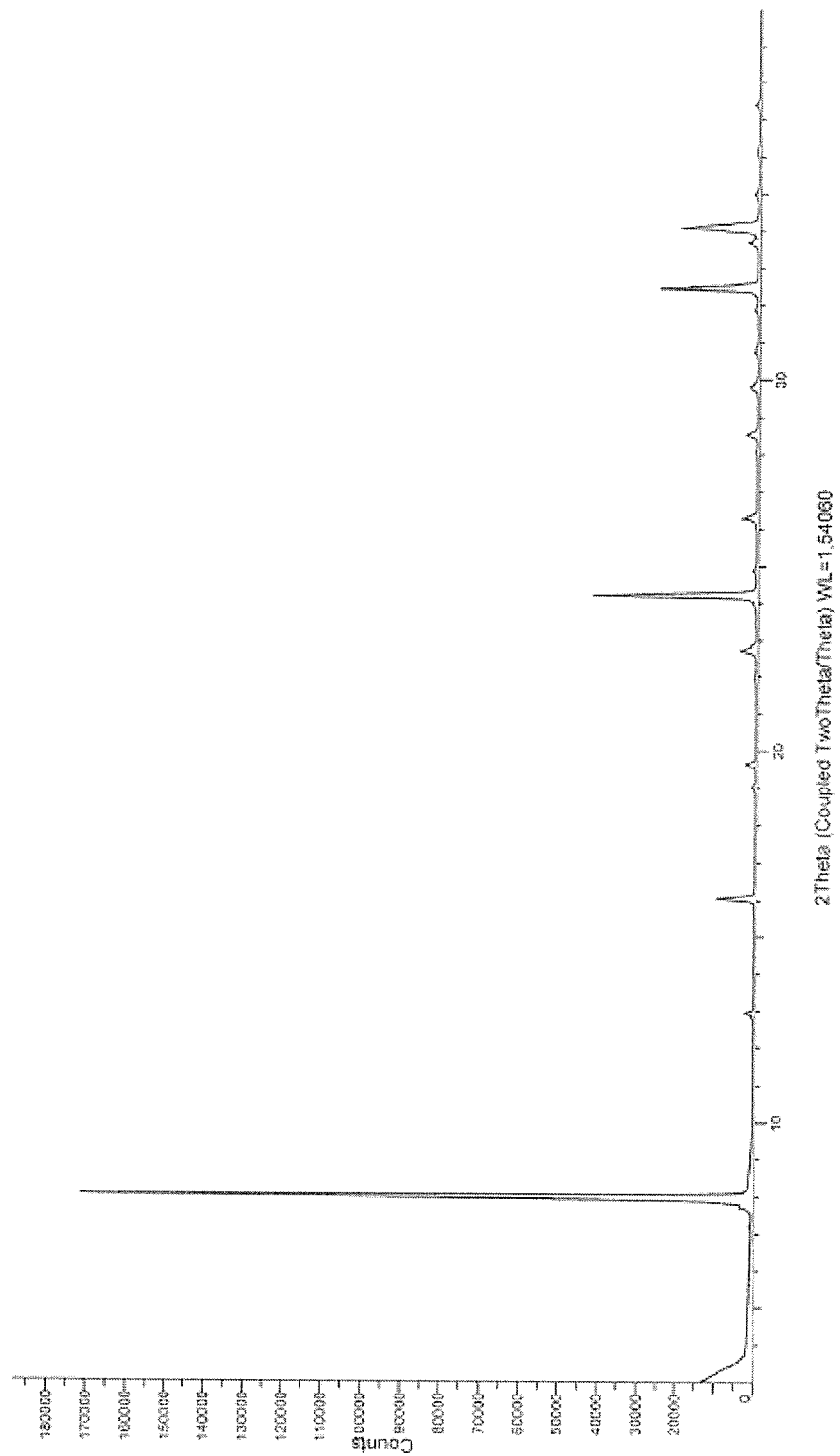

ISOLATION AND PURIFICATION OF 6-AMINOCAPROIC ACID

FIELD OF THE INVENTION

The present invention relates to a new process for the isolation and purification of 6-aminocaproic acid, which is a known inhibitor of enzymes responsible for fibrinolysis and is used in the treatment of coagulopathies and severe post-operative bleedings.

BACKGROUND 6-aminocaproic acid of formula (I) is commonly used for the preparation of plastic materials, but it is also used as medicine for the treatment of coagulopathies and severe post-operative bleedings. The drug is currently commercialized by Clover Pharmaceuticals Corp. with the brand name Amicar®, both as solutions for oral use (0.25 g/mL) and as tablets (500 mg or 1000 mg).

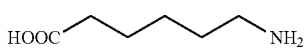
(I)

6-aminocaproic acid of formula (I) used in the polymer industry makes it a compound readily available at a low cost, but the product necessary for medical use has not the quality to be suitable as active pharmaceutical ingredient.

The synthesis of 6-aminocaproic acid is known for a while and is generally carried out by hydrolyzing caprolactam of formula (II).

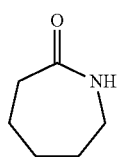
(II)

The reaction can be carried out under acidic or basic conditions and there are no major reactivity issues. At the end of the hydrolysis a solution of a 6-aminocaproic acid salt is obtained and the desired product is isolated by neutralizing the mixture, which provides the free amino acid.

However, the isolation of the 6-aminocaproic acid of formula (I) as such is rather challenging, because 6-aminocaproic acid is a very polar molecule with a high solubility in water. Due to these properties the liquid/liquid extraction with an organic solvent after the hydrolysis and neutralization results in the best situations to a partial extraction into the organic phase, but more commonly the product remains totally in the aqueous phase. By concentrating the neutralized solution it is possible to isolate the 6-aminocaproic acid by precipitation, but the precipitate is contaminated with inorganic salts formed during the neutralization.

Different approaches have been disclosed for obtaining a product with a greater purity. For example, Meyers and Miller describe in Organic Syntheses, Coll. Vol. 4, p. 39 (1963) that the 6-aminocaproic acid hydrochloride salt of formula (Y)

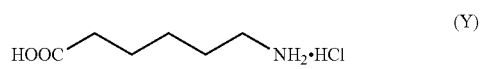
(Y)

can be released by ion exchange chromatography. However, this process is not suitable for industrial applications, because it is well known that ion exchange chromatography is particularly expensive and labor intensive due to the use of the resins.

In Organic Syntheses, Coll. Vol. 2, p. 28 (1943) the hydrochloride salt of 6-aminocaproic acid of formula (Y) is converted into the 6-aminocaproic acid of formula (I) by treating the aqueous solution with lead oxide, lead hydroxide, and silver oxide, and finally sulfuric acid in order to remove all metal ions and halogenates.

U.S. Pat. No. 3,655,748 discloses that the hydrolysis of caprolactam of formula (II) is carried out in presence of barium hydroxide. At the end of the reaction the solution is neutralized by adding $CO_2$, and the formed barium carbonate precipitate is filtered off and removed quantitatively from the solution. The aqueous solution, which comprises only 6-aminocaproic acid of formula (I), is then concentrated providing 6-aminocaproic acid of formula (I) as solid.

The method described in U.S. Pat. No. 8,809,581 seeks to solve the above cited issue of the workup by treating the reaction mixture of the hydrolyzed caprolactam of formula (II) with a reagent able to introduce a protecting group, which can be removed afterwards by hydrogenation. By this way, the protected 6-aminocaproic acid has a good solubility in organic solvents, thus can be extracted into the organic phase and then finally deprotected by hydrogenation. However, this procedure comprises a further synthetic step in the production process and the use of palladium based catalysts in the last step of the synthesis. In this process it is necessary to completely remove the catalyst in order to guarantee the absence of heavy metals in the final product.

Thus, there is still the need to have a more suitable alternative method for isolating and purifying 6-aminocaproic acid of formula (I).

The inventors of the present invention have surprisingly found that the purification of 6-aminocaproic acid of formula (I) can be performed effectively, also at an industrial scale, by removing the addition salt of 6-aminocaproic acid of formula (Ia), as herein defined, by an organic base in a solvent. The new method results to be advantageous in respect to the procedures known in the art, since it is industrially scalable, it does not comprise the use or the formation of toxic compounds, nor the use of ion exchange resins or heavy metals, and the 6-aminocaproic acid of formula (I) obtained by this procedure contains a minimal amount of impurities, in particular the one of formula (III) as described below.

SHORT DESCRIPTION OF THE FIGURE AND THE ANALYTICAL METHODS

The hydrochloride salt of 6-aminocaproic acid in crystalline form, herein designed as Form A, was characterized by X-ray powder diffraction (XRPD). The X-ray diffraction spectra (XRPD) were produced by a Bruker D8 Advance diffractometer. The employed detector was PSD LynxEye detector and the sample was irradiated with Nickel filtered Cu Kα. The X ray diffraction spectra data were collected in the range 2θ from 3° to 40° with a step size of 0.02°.

The aqueous content of the hydrochloride salt of 6-aminocaproic acid in crystalline form, herein designed as Form A, was around 0.10% and was determined by Karl Fischer titration.

FIG. 1 shows the XRPD spectrum of the hydrochloride salt of 6-aminocaproic acid in crystalline form, herein designed as Form A, wherein the most intense peaks, expressed as ° in 2θ, are to be found at about: 7.99, 12.93, 16.06, 19.02, 19.64, 21.99, 22.74, 24.21, 24.87, 26.30, 28.08, 28.53, 29.81, 30.72, 31.82, 32.49, 33.70, 34.10, 34.97, and 36.15 (±0.2).

SUMMARY OF THE INVENTION

The present invention relates to a new process for the isolation and purification of 6-aminocaproic acid of formula (I), comprising

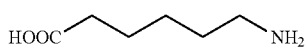

(I)

formation of a mixture of an addition salt of 6-aminocaproic acid of formula (Ia) with a protic acid, in a solvent,

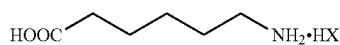

(Ia)

wherein HX is a protic acid;
conversion of said salt into 6-aminocaproic acid of formula (I) by treatment with an organic base in a solvent, and recovery the 6-aminocaproic acid of formula (I) from said mixture.

DETAILED DESCRIPTION OF THE INVENTION

Object of the present invention is a process for the isolation and purification of 6-aminocaproic acid of formula (I), comprising

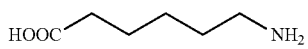

(I)

formation of a mixture of an addition salt of 6-aminocaproic acid of formula (Ia) with a protic acid, in a solvent,

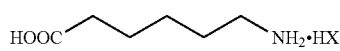

(Ia)

wherein HX is a protic acid,
conversion of said salt into 6-aminocaproic acid of formula (I) by treatment with an organic base in a solvent, and recovery of the 6-aminocaproic acid of formula (I) from said mixture.

The addition salt of 6-aminocaproic acid with a protic acid of formula (Ia) is typically a pharmaceutically acceptable salt, in a solid state form, typically in crystalline or amorphous, solvate or hydrate form.

According to a preferred feature of the invention, the addition salt is the hydrochloride salt in the novel crystalline form, herein designed as Form A.

The employed protic acid of formula HX, used for the salification of the 6-aminocaproic acid can be a mineral or an organic acid.

A mineral acid can be for example chosen from the group comprising sulfuric acid, phosphoric acid and a hydrohalic acid, preferably hydrochloric acid.

An organic acid can be for example chosen from the group comprising a sulfonic acid, typically camphorsulfonic acid, p-toluenesulfonic acid, methanesulfonic acid or trifluoromethanesulfonic acid; an aryl carboxylic acid, typically a benzoic acid; a $C_1$-$C_4$ alkyl-carboxylic acid, wherein the $C_1$-$C_4$ alkyl group, which can be straight or branched, is optionally substituted by one or more halogen atoms, preferably from one to three chloro or fluoro atoms, typically acetic acid or trifluoroacetic acid.

A mixture of an addition salt of 6-aminocaproic acid of formula (Ia) with a protic acid can be prepared, for instance, by a process comprising:
1) adding a protic acid of formula (HX), as defined above, to a mixture of 6-aminocaproic acid of formula (I) in a solvent, as defined herein; or
2) mixing an addition salt of 6-aminocaproic acid of formula (Ia) in a solvent as defined herein; or
3) reacting a precursor of the 6-aminocaproic acid in presence of a protic acid of formula (HX) and a solvent as defined herein.

According to the alternative 1), adding a protic acid of formula (HX), as defined above, to a mixture of 6-aminocaproic acid of formula (I) in a solvent, as defined herein, can be performed according to known methods.

According to the second alternative 2), a mixture of an addition salt of the 6-aminocaproic acid of formula (Ia) in a solvent can be obtained by mixing an addition salt of 6-aminocaproic acid of formula (Ia) in a solvent as defined herein.

A mixture of an addition salt of the 6-aminocaproic acid of formula (Ia) in a solvent, obtained by above methods, can be optionally heated to a temperature ranging from about 25° C. to about the reflux temperature of the solvent in order to improve the solubility of the salt or for a better stirring of the reaction mixture.

According to the last alternative 3), a precursor of the 6-aminocaproic acid is preferably a straight or branched ester or amide of the 6-aminocaproic acid, for instance a caprolactam of formula (II), as defined above.

According to said alternative 3), a salt of 6-aminocaproic acid of formula (Ia) can be preferably obtained by hydrolyzing a caprolactam of formula (II) under acidic conditions, for instance performing the hydrolysis of the caprolactam of formula (II) by treatment with hot concentrated hydrochloric acid and concentrating the mixture at the end of the reaction.

The salt of formula (Ia), obtained by each of the above alternative methods, can be optionally further re-crystallized in order to increase its purity, according to procedures well known in art, for instance optionally using a seed crystal previously obtained.

A further aspect of the invention relates to the hydrochloride salt of 6-aminocaproic acid of formula (Ia) in crystalline form, herein designed as Form A, obtained by the above process, having an aqueous content of around 0.10%, as determined by Karl Fischer titration, and having an XRPD spectrum, wherein the most intense peaks, expressed as ° in 2θ, are to be found at about: 7.99, 12.93, 16.06, 19.02, 19.64, 21.99, 22.74, 24.21, 24.87, 26.30, 28.08, 28.53, 29.81, 30.72, 31.82, 32.49, 33.70, 34.10, 34.97, and 36.15 (±0.2), as shown in the FIG. 1.

An organic base for the conversion of the salt of formula (Ia) into the 6-aminocaproic acid of formula (I) is preferably a nitrogen containing organic base, for example ammonia or a primary, secondary or tertiary amine, for example triethylamine o tributylamine.

The organic base can be used in about stoichiometric amounts or in excess with respect to the moles of 6-aminocaproic salt of formula (Ia) to be unblocked, preferably in over-stoichiometric amounts, for example in amounts ranging from about 1.0 to 10 equivalents with respect to the salt. In a preferred aspect of the invention the organic base is used in an amount ranging from about 1.0 to about 2.0 equivalents with respect to the 6-aminocaproic salt of formula (Ia).

The organic base can be added to the mixture of the 6-aminocaproic salt of formula (Ia) as such or dissolved (diluted) in a solvent. After the addition of the base the mixture can be optionally heated to a temperature ranging from about 25° C. to about the reflux temperature of the solvent in order to improve the solubility of all components of the mixture.

A solvent that can be used both for obtaining a mixture of a salt addition of 6-aminocaproic salt of formula (Ia) with a protic acid, and for converting an addition salt of 6-aminocaproic salt of formula (Ia) into 6-aminocaproic acid of formula (I), and for the optional dilution of the organic base, can be a solvent selected from the group comprising a polar aprotic solvent, for example dimethylformamide, dimethylsulfoxide or acetonitrile; an ethereal solvent, for example diethylether, methyl tert-butyl ether or tetrahydrofurane; a ketone, for example methylethylketone, methylisobutylketone or acetone; an apolar aprotic solvent, for example hexane, heptane, toluene or xylene; a polar protic solvent, for example a branched or straight $C_1$-$C_5$ alkanol, a $C_1$-$C_4$ alkyl carboxylic acid as defined previously, and water; or a mixture of two or more, for example two or three, of said solvents.

The mixture obtained after treatment with a base shows typically a title of the 6-aminocaproic acid of formula (I) ranging from about 5 wt. % to about 90 wt. %, preferably ranging from about 5 wt. % to about 70 wt. %, more preferably from about 10 wt. % to about 30 wt. %.

The recovery and the isolation from the obtained mixture of the 6-aminocaproic salt of formula (I), for example as solid, can be achieved by crystallization.

The crystallization can be supported by cooling the reaction mixture, or by concentration by removing the solvent under vacuum, or by seeding with a seed crystal previously obtained, or by performing more than one of the above steps. The crystallization can be further supported by adding a solvent from those defined previously, wherein the aminocaproic acid of formula (I), is poorly soluble.

The obtained solid 6-aminocaproic acid of formula (I) can be isolated from the crystallization mixture by filtration or centrifugation according to methods well known in the art. The obtained solid 6-aminocaproic acid of formula (I) can be optionally re-crystallized according to methods well known in the art in order to increase the purity of the product.

The 6-aminocaproic acid of formula (I) obtained by the isolation and purification as disclosed in present invention has a chemical purity equal to or higher than 99.0%, preferably equal to or more than 99.8%, more preferably equal to or more than 99.96% calculated as Area % (A %) by HPLC at 210 nm.

In particular, the 6-aminocaproic acid of formula (I) obtained by the process of the present invention, comprises a compound of formula (III), which is a side product of the synthesis of the 6-aminocaproic acid of formula (I), in amounts equal to or lower than 0.1%, preferably equal to or lower than 0.08%, more preferably equal to or lower than 0.01%, calculated by Area % (A %) HPLC at 210 nm.

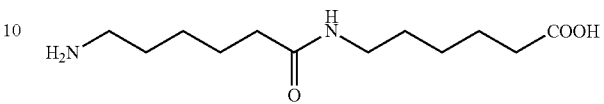

(III)

A further aspect of the invention relates to a mixture comprising 6-aminocaproic acid of formula (I) and a compound of formula (III) in amounts equal to or lower than 0.1%, preferably equal to or lower than 0.08%, more preferably equal to or lower than 0.01%, calculated by Area % (A %) HPLC at 210 nm, in particular as a pharmaceutical composition comprising 6-aminocaproic acid of formula (I), as active ingredient, a compound of formula (III) in amounts equal to or lower than 0.1%, preferably equal to or lower than 0.08%, more preferably equal to or lower than 0.01%, calculated by A % HPLC at 210 nm, and a pharmaceutically acceptable excipient and/or carrier.

Such pharmaceutical composition, having the same dosage of the approved drug product can for example be for injectable or oral administration, for instance as tablet or syrup, and prepared according to the methods known in the art.

Another aspect of the invention relates to a process for the preparation of a mixture comprising 6-aminocaproic acid of formula (I) and the compound of formula (III) in amounts equal to or lower than 0.1%, preferably equal to or lower than 0.08%, more preferably equal to or lower than 0.01%, calculated by Area % (A %) HPLC at 210 nm, said process comprising the method of isolation and purification of the present invention.

The following examples further illustrate the invention.

Example 1

Synthesis of a Hydrochloride Salt of 6-Aminocaproic Acid of Formula (Ia) by Hydrolysis of Caprolactam of Formula (II)

160.0 g of caprolactam and 344 g of HCl 37 wt. %. are placed at room temperature and under nitrogen atmosphere in a reactor comprising a mechanical stirrer, a reflux condenser and a trap containing NaOH 10 wt. % and the stirred mixture is heated to 90° C. After 15 hours 480 mL of toluene are added and a Dean-Stark trap is mounted. The mixture is vigorously stirred and the water is removed by azeotropic distillation. Optionally, a seed crystal of 6-aminocaproic acid is added and a crystalline solid is formed. After complete removal of the water, the mixture is cooled down to 20° C. in about 6 hours. After one night, the solid filtered off, rinsed with toluene and dried at 50° C. at a reduced pressure providing 233 g of the hydrochloride salt of the 6-aminocaproic acid of formula (Ia) in a crystalline form (yield: 98%). HPLC at 210 nm, title: 99.2%, purity HPLC at 210 nm: 95.0%; presence of impurity (III): 0.25% in A %.

The hydrochloride salt of 6-aminocaproic acid of formula (Ia) in crystalline form, herein designed as Form A, obtained by the above process has an aqueous content of around 0.10%, as determined by Karl Fischer titration, and has an XRPD spectrum, wherein the most intense peaks, expressed as ° in 2θ, are to be found at about: 7.99, 12.93, 16.06, 19.02, 19.64, 21.99, 22.74, 24.21, 24.87, 26.30, 28.08, 28.53, 29.81, 30.72, 31.82, 32.49, 33.70, 34.10, 34.97, and 36.15 (±0.2), as shown in FIG. 1.

Example 2

Synthesis of 6-Aminocaproic Acid of Formula (I) Starting from the Hydrochloride Salt of 6-Aminocaproic Acid of Formula (Ia)

60.0 g of the hydrochloride salt of the 6-aminocaproic acid of formula (Ia), as prepared in Example 1, and 276 mL of methanol are placed at 20° C. and under nitrogen atmosphere in a reactor comprising a mechanical stirrer and a thermometer. 16.3 mL of triethylamine are added within about 30 minutes to the stirred solution, which is then seeded with 6-aminocaproic acid. After 2 hours under stirring, the remaining 38.6 mL of triethylamine are added within 5 hours. The mixture is stirred for further 10 hours at 20° C., then the solid is filtered off, washed with methanol and dried at 50° C. at a reduced pressure providing 39.2 g of 6-aminocaproic acid of formula (I) as a white solid (Yield: 83%). HPLC Title at 210 nm: 100.6%, purity HPLC at 210 nm: 99.8%; presence of impurity (III): 0.19% in A %. Argentometric titration: chloride content 0.16%

Example 3

Recrystallization of 6-Aminocaproic Acid of Formula (I)

35.0 g of 6-aminocaproic acid of formula (I), as prepared in Example 2, and 210 mL of methanol are placed at room temperature and under nitrogen atmosphere in a reactor comprising a mechanical stirrer, a reflux condenser and a thermometer. The mixture is heated to reflux, and 35 mL of water is added stepwise to completely dissolve the product. The clear solution is then brought to 50° C. and seeded with 6-aminocaproic acid. 175 mL of acetone are added over 3 hours and the mixture is kept at 50° C. for 1 hour, then cooled down to 20° C. in 3 hours. After stirring overnight, the solid is filtered off, washed with methanol and dried at 50° C. at a reduced pressure providing 31.0 g of 6-aminocaproic acid of formula (I) as a white solid (Yield: 88%). HPLC Title at 210 nm: 98.9%, purity HPLC at 210 nm: 99.8%; presence of impurity (III): 0.08% in A %. Argentometric titration: chloride content 0.04%

Example 4

Recrystallization of the Hydrochloride Salt of 6-Aminocaproic Acid of Formula (Ia)

100.0 g the hydrochloride salt of the 6-aminocaproic acid of formula (Ia), as prepared in Example 1, and 300 mL of isopropanol are placed at room temperature and under nitrogen atmosphere in a reactor comprising a mechanical stirrer, a reflux condenser and a thermometer. The mixture is heated to reflux until the product is completely dissolved. The solution is then brought to 80° C., kept at the same temperature for 2 hours and then cooled down to 0° C. in 9 hours. After 2 hours stirring at 0° C. the solid is filtered off, washed with isopropanol and dried at 50° C. at a reduced pressure providing 92.0 g of the hydrochloride salt of the 6-aminocaproic acid of formula (Ia) as a white solid and in a crystalline form (yield: 92%).

HPLC Title at 210 nm: 100.3%, purity HPLC at 210 nm: 99.98%; presence of impurity (III): 0.01% in A %.

The hydrochloride salt of 6-aminocaproic acid of formula (Ia) in crystalline form, herein designed as Form A, obtained by the above process has an aqueous content of up to around 0.10%, as determined by Karl Fischer titration, and has an XRPD spectrum, wherein the most intense peaks, expressed as ° in 2θ, are to be found at about: 7.99, 12.93, 16.06, 19.02, 19.64, 21.99, 22.74, 24.21, 24.87, 26.30, 28.08, 28.53, 29.81, 30.72, 31.82, 32.49, 33.70, 34.10, 34.97, and 36.15 (±0.2), as reported in the FIG. 1.

Example 5

Synthesis of 6-Aminocaproic Acid of Formula (I) Starting from the Hydrochloride Salt of 6-Aminocaproic Acid of Formula (Ia)

60.0 g of the hydrochloride salt of the 6-aminocaproic acid of formula (Ia), as prepared in Example 4, are converted into the 6-aminocaproic acid of formula (I) following the same procedure as described in Example 2 providing 39.3 g of 6-aminocaproic acid of formula (I) as white solid (Yield: 84%). HPLC Title at 210 nm: 99.5%, purity HPLC at 210 nm: 99.96%; presence of impurity (III): 0.01% in A %. Argentometric titration: chloride content 0.15%.

Example 6

Synthesis of 6-Aminocaproic Acid of Formula (I) Starting from the Hydrochloride Salt of 6-Aminocaproic Acid of Formula (Ia) Using Tri-n-Butyl Amine as Base 5.0 g of the hydrochloride salt of the 6-aminocaproic acid of formula (Ia), as prepared in Example 1, are converted into the 6-aminocaproic acid of formula (I) following the same procedure as described in Example 2 with the exception of using 1.2 equivalents (6.63 g) of tributylamine instead of TEA as base and acetonitrile instead of methanol as solvent. After 2 hours of incubation time the workup was carried out as described in Example 2 providing 3.82 g of 6-aminocaproic acid of formula (I) as white solid (Yield: 97.7%). HPLC Title at 210 nm: 92.4%, purity HPLC at 210 nm: 99.92%

The invention claimed is:
1. A process for preparing 6-aminocaproic acid of formula (I),

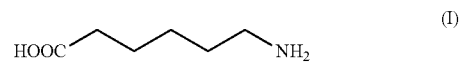

comprising
mixing an addition salt of 6-aminocaproic acid of formula (Ia) with a protic acid and a solvent to produce a mixture,

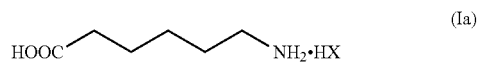

wherein HX is a protic acid,
adding an organic base to said mixture to convert said addition salt of 6-aminocaproic acid into 6-aminocaproic acid of formula (I) and
recovering the 6-aminocaproic acid of formula (I) from said mixture by crystallization.

2. The process of claim 1, wherein the addition salt of formula (Ia) is a pharmaceutically acceptable salt, in crystalline or amorphous, solvate or hydrate form.

3. The process of claim 1, wherein the protic acid of formula HX is a mineral acid selected from the group consisting of sulfuric acid, phosphoric acid and a hydrohalic acid; or an organic acid selected from the group consisting of a sulfonic acid; an aryl carboxylic acid, and a $C_1$-$C_4$ alkyl-carboxylic acid, wherein the $C_1$-$C_4$ alkyl group is straight or branched, and is unsubstituted or substituted by one to three chloro or fluoro atoms.

4. The process of claim 1, wherein the protic acid is hydrochloric acid.

5. The process of claim 1, wherein the addition salt of 6-aminocaproic acid of formula (Ia) with a protic acid is prepared by:
1) adding a protic acid of formula HX, to a mixture of 6-aminocaproic acid of formula (I) in a solvent; or
2) reacting a precursor of the 6-aminocaproic acid in the presence of a protic acid of formula HX and a solvent.

6. The process of claim 5, wherein the precursor of a 6-aminocaproic acid is caprolactam of formula (II)

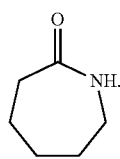

(II)

7. The process of claim 5, wherein the salt of formula (Ia), is further re-crystallized, optionally using a seed crystal previously obtained.

8. The process of claim 1, wherein the organic base is a nitrogen containing organic base.

9. The process of claim 8, wherein the base is ammonia or a primary, secondary or tertiary amine.

10. The process of claim 8, wherein the base is triethylamine or tributylamine.

11. The process of claim 8, wherein the base is used in about stoichiometric amounts or in excess with respect to the moles of 6-aminocaproic salt of formula (Ia) to be unblocked.

12. The process of claim 8, wherein the base is added to the mixture of the 6-aminocaproic salt of formula (Ia) as such or dissolved (diluted) in a solvent.

13. The process of claim 1, wherein the solvent is selected from the group consisting of a polar aprotic solvent; an ethereal solvent; a ketone; an apolar aprotic solvent; a polar protic solvent; water; and a mixture of two or three of said solvents.

14. The process of claim 13, wherein the solvent is selected from methanol and acetonitrile.

15. The process of claim 1, wherein the recovering of 6-aminocaproic acid of formula (I) from the mixture is performed by crystallization followed by filtration and/or centrifugation.

* * * * *